(12) United States Patent
Sinibaldi et al.

(10) Patent No.: US 10,675,755 B2
(45) Date of Patent: Jun. 9, 2020

(54) SHAPE-KEEPING DEPLOYABLE STRUCTURE INCLUDING A PAIR OF ROBOTIC SYSTEMS OF THE CONTINUUM TYPE

(71) Applicant: FONDAZIONE ISTITUTO ITALIANO DI TECNOLOGIA, Genoa (IT)

(72) Inventors: Edoardo Sinibaldi, Genoa (IT); Byungjeon Kang, Genoa (IT); Risto Kojcev, Genoa (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 147 days.

(21) Appl. No.: 15/570,319

(22) PCT Filed: Apr. 27, 2016

(86) PCT No.: PCT/IB2016/052396
§ 371 (c)(1),
(2) Date: Oct. 27, 2017

(87) PCT Pub. No.: WO2016/174596
PCT Pub. Date: Mar. 11, 2016

(65) Prior Publication Data
US 2018/0125593 A1 May 10, 2018

(30) Foreign Application Priority Data

Apr. 27, 2015 (IT) .............................. TO2015A0233

(51) Int. Cl.
*B25J 9/10* (2006.01)
*A61B 1/01* (2006.01)
(Continued)

(52) U.S. Cl.
CPC ........... *B25J 9/1085* (2013.01); *A61B 1/0016* (2013.01); *A61B 1/0057* (2013.01); *A61B 34/71* (2016.02); *A61B 2034/301* (2016.02)

(58) Field of Classification Search
CPC ... B25J 9/0027; B25J 9/06; B25J 9/065; B25J 9/104; B25J 9/105; B25J 9/1085;
(Continued)

(56) References Cited

U.S. PATENT DOCUMENTS 5,662,587 A * 9/1997 Grundfest .......... A61B 1/00082
600/114
6,036,636 A 3/2000 Motoki et al.
(Continued)

FOREIGN PATENT DOCUMENTS

CA  2900314 A1 * 8/2014 ............. A61B 17/29
EP  2 446 803 A1  5/2012

OTHER PUBLICATIONS

PCT Notification of Trarismittal of the International Search Report and the Written Opinion of the International Searching Authority, or the Declaration for PCT Counterpart Application No. PCT/IB2016/052396 Containing International Search Report, 11 pgs. (dated Aug. 18, 2016).

*Primary Examiner* — Bobby Rushing, Jr.
(74) *Attorney, Agent, or Firm* — Womble Bond Dickinson (US) LLP (57) ABSTRACT

A deployable structure is described including a first and a second robotic system (4, 6; 604, 606), each of which includes: a respective distal element (12;22); at least one respective shape-locking element (14;24); and a respective coupling structure (16;26) operable in a first and a second operating mode. When the coupling structure of the first robotic system operates in the first operating mode, it is elastically deformable and operable so as to move the first robotic system; when the coupling structure of the first
(Continued)

robotic system operates in the second operating mode, it forms a guide for the movement of the second robotic system. When the coupling structure of the second robotic system operates in the first operating mode, it is elastically deformable and is operable so as to move the second robotic system; when the coupling structure of the second robotic system operates in the second operating mode, it forms a guide for the movement of the shape-locking element of the first robotic system.

15 Claims, 7 Drawing Sheets

(51) Int. Cl.
  *A61B 1/00* (2006.01)
  *A61B 1/005* (2006.01)
  *A61B 34/00* (2016.01)
  *A61B 34/30* (2016.01)
(58) Field of Classification Search
  CPC . A61B 34/71; A61B 2034/301; A61B 1/0055; A61B 1/0057
  USPC .......................................... 74/490.04; 901/21
  See application file for complete search history.

(56) References Cited

U.S. PATENT DOCUMENTS

| | | | |
|---|---|---|---|
| 6,450,104 B1* | 9/2002 | Grant | B08B 9/049 104/138.1 |
| 7,044,245 B2* | 5/2006 | Anhalt | B08B 9/045 180/9.1 |
| 7,365,509 B2* | 4/2008 | Park | A61B 1/00156 318/568.12 |
| 7,744,619 B2* | 6/2010 | Eidenschink | A61F 2/856 604/96.01 |
| 8,523,763 B2* | 9/2013 | Sinai | A61B 1/00082 600/116 |
| 2001/0053874 A1 | 12/2001 | Pauker | |
| 2011/0295065 A1 | 12/2011 | Gurusamy et al. | |
| 2013/0090763 A1* | 4/2013 | Simaan | A61B 5/11 700/258 |
| 2014/0148673 A1* | 5/2014 | Bogusky | A61M 25/0052 600/374 |

* cited by examiner

SHAPE-KEEPING DEPLOYABLE STRUCTURE INCLUDING A PAIR OF ROBOTIC SYSTEMS OF THE CONTINUUM TYPE

CROSS-REFERENCE TO RELATED APPLICATIONS

This patent application is a U.S. National Phase Application under 35 U.S.C. § 371 of International Application No, PCT/IB2016/052396, filed Apr. 27, 2016, entitled A SHAPE-KEEPING DEPLOYABLE STRUCTURE INCLUDING A PAIR OF ROBOTIC SYSTEMS OF THE CONTINUUM TYPE, which claims priority to Italian Patent Application No. TO2015A000233, filed Apr. 27, 2015.

TECHNICAL FIELD

The present invention refers to a shape-keeping deployable probe, which includes a pair of robotic systems of the continuum type.

BACKGROUND ART

As is known, today the need for deployable structures, able to follow curvilinear trajectories, is particularly felt. Said need is particularly felt, for example, in the biomedical field, where probes are required able to follow curved trajectories inside the human body, or in the field of contactless inspections.

In greater detail, the need is felt for deployable structures which can be operated in such a way that the desired trajectory is followed not only by a distal end of the structure, but also by the body of the structure, as it is deployed. In other words, it is desirable for the proximal sections of a deployable structure to follow the same trajectory as the one followed previously by the distal portions; generally, this capacity is referred to as follow-the-leader, i.e. the distal end, or also as shape-keeping, i.e. the trajectory followed by the distal end. Furthermore, it is desirable for the follow-the-leader capacity to be intrinsic to the deployable structure, i.e. not exploit the characteristics of the environment in which the structure operates.

For example, the patent application EP2446803 describes an articulated robotic probe, which includes a first and a second mechanism arranged concentrically, each of which can be directed in desired directions; furthermore, each mechanism comprises a plurality of rigid cylindrical arms, interconnected by means of spherical joints, and is controlled alternatively in a first mode, in which it is rigid as a whole, and in a second mode, in which the arms are mobile with respect to one other.

The robotic probe according to the patent application EP2446803 is intrinsically of the follow-the-leader type, however its capacity for faithfully following a predetermined trajectory is limited, since it is of the articulated type. Furthermore, when one of the two mechanisms runs in the area of the joints of the other mechanism, undesired vibrations are generated.

The patent application US2001/0053874 describes an endoscope comprising a distal terminal portion, of movable type, and an operating device, which is operatively connected to the distal terminal portion, to operate the latter. The patent application US 2011/0295065 describes a segmented instrument having an elongated body, which includes a plurality of connections and a hinge which connects a pair of adjacent connections of said plurality of connections.

Lastly, the U.S. Pat. No. 6,036,636 describes an endoscope including an elastic member, which connects a distal terminal portion of an insertion portion to a proximal terminal portion of a tip portion, so as to form a space portion. A wire extends from the tip portion to a proximal side of the insertion portion and is curved in the space portion.

SUMMARY

The object of the present invention is therefore to provide a deployable structure which solves at least partly the drawbacks of the known art.

According to the invention, a deployable structure is provided as defined in the attached claims.

BRIEF DESCRIPTION OF THE DRAWINGS

For a better understanding of the invention, embodiments thereof are now described, purely by way of non-limiting example and with reference to the attached drawings, in which.

DETAILED DESCRIPTION

Figure 1:
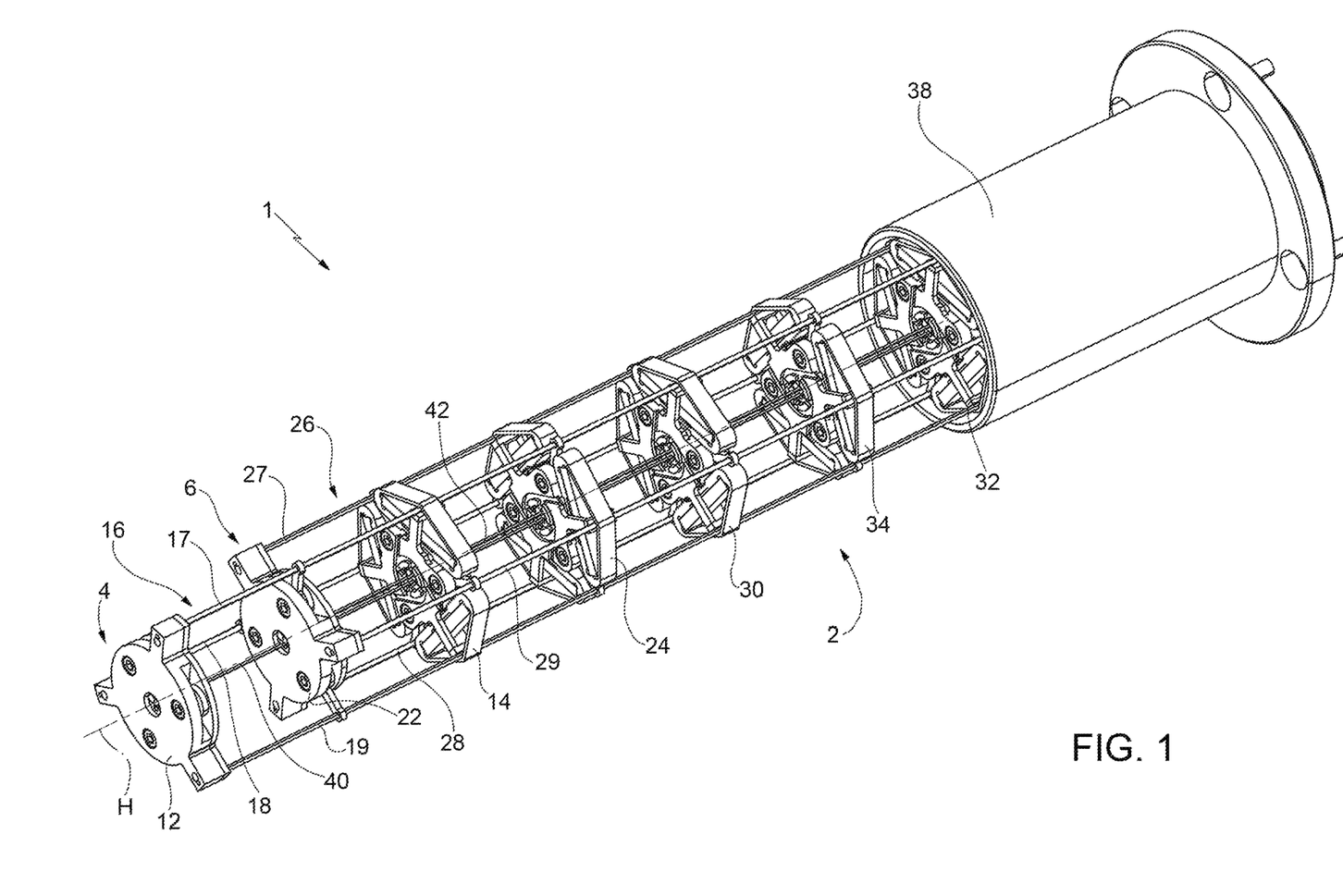
FIG. 1 shows a perspective view of a portion of an embodiment of the present deployable structure.

FIG. 1 shows a deployable system 1, which comprises a deployable probe 2, which in turn comprises a first and a second robotic system 4, 6, both of the continuum type.

In detail, the first robotic system 4 comprises a first distal element 12 and at least one first shape-locking element 14. The second robotic system 6 comprises a respective distal element 22, referred to below as the second distal element 22, and at least one respective shape-locking element 24, referred to below as the second shape-locking element 24. Without any loss of generality, FIG. 1 shows overall three shape-locking elements of the first robotic system 4 and two shape-locking elements of the second robotic system 6. In particular, the first robotic system 4 comprises, in addition to the first shape-locking element 14, a third and a fourth shape-locking element 30, 32; furthermore, the second robotic system 6 comprises, in addition to the second shape-locking element 24, a fifth shape-locking element 34 and a sixth shape-locking element, the latter not being visible in FIG. 1 since it is housed inside a housing structure 38 adapted to house the first and the second robotic system 4, 6, when the deployable structure 2 is retracted.

The first robotic system 4 further comprises a first coupling structure 16, which mechanically couples the first distal element 12 to the shape-locking elements of the first robotic system 4, and in particular to the first shape-locking element 14.

The first coupling structure 16 comprises a first, a second and a third rod 17, 18, 19, which in the embodiment shown in FIG. 1 have a cylindrical shape. Each first, second and third rod 17, 18, 19 has a respective end fixed to the first distal element 12 and is coupled to each first, third and fourth shape-locking element 14, 30, 32 in such a way as to be alternatively slidable relative to it, or fixed relative to it, as described in further detail below, with particular reference, for the sake of brevity, only to the first shape-locking element 14.

The second robotic system 6 comprises a second coupling structure 26, which mechanically couples the second distal element 22 to the shape-locking elements of the second robotic system 6, and in particular to the second shape-locking element 24.

The second coupling structure 26 comprises a fourth, a fifth and a sixth rod 27, 28, 29, which in the embodiment shown in FIG. 1 have a cylindrical shape. Each fourth, fifth and sixth rod 27, 28, 29 has a respective end fixed to the second distal element 22 and is coupled to each second, fifth and sixth shape-locking element 24, 34 so as to be alternatively slidable relative to it, or fixed relative to it, as described in further detail below, with particular reference, for the sake of brevity, only to the second shape-locking element 24.

The first robotic system 4 also comprises a first connection cable 40, which has a respective end, which is fixed to the first distal element 12; furthermore the first connection cable 40 is fixed to each shape-locking element of the first robotic system 4. In this regard, the deployable system 1 is such that the section of the first connection cable 40 between the first distal element 12 and the first shape-locking element 14, in addition to the sections of the first connection cable 40 between adjacent pairs of shape-locking elements of the first robotic system 4, all have the same length $L_{max}$.

The second robotic system 6 further comprises a second connection cable 42, which has a respective end, which is fixed to the second distal element 22; furthermore the second connection cable 42 is fixed to each of the shape-locking elements of the second robotic system 6. In said regard, the deployable system 1 is such that the section of the second connection cable 42 between the second distal element 22 and the second shape-locking element 24, in addition to the section of the second connection cable 42 between adjacent pairs of shape-locking elements of the second robotic system 6, all have the above-mentioned length $L_{max}$.

In further detail, the first and the second robotic system 4, 6 have respective axes of symmetry, which coincide with each other and form an axis of symmetry H of the deployable structure 2. Furthermore, the first and the second robotic system 4, 6 are interlaced with each other; in particular, along the axis of symmetry H, the first distal element 12, the second distal element 22, the first shape-locking element 14, the second shape-locking element 24, the third shape-locking element 30, the fifth shape-locking element 34, the fourth shape-locking element 32 and the sixth shape-locking element follow each other in the above order.

Without any loss of generality, the shape-locking elements of the first and second robotic system 4, 6 are identical. Furthermore, the shape-locking elements of the first robotic system 4, and in particular the first shape-locking element 14, have the same first orientation relative to the axis of symmetry H, while the shape-locking elements of the second robotic system 6, and in particular the second shape-locking element 24, have the same second orientation with respect to the axis of symmetry H; the first and the second orientation differ from each other by 180°. In other words, the second shape-locking element 24 is angularly staggered relative to the first shape-locking element 14 by an angle of 180°, in such a way that, as described below, there is a rest condition in which the first, second, third, fourth, fifth and sixth rod 17, 18, 19, 27, 28, 29 extend straight. For the sake of brevity, below only the first shape-locking element 14 is described in detail.

Figure 2:
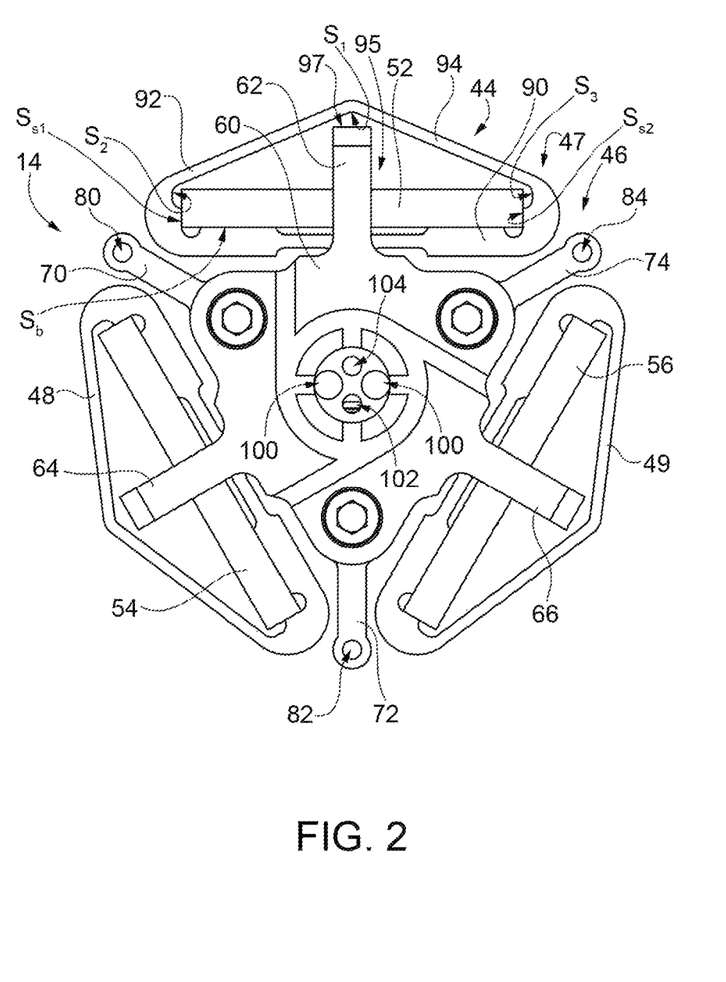
FIGS. 2, 4, 5, 6 show front views of components of the deployable structure shown in FIG. 1.
Figure 3:
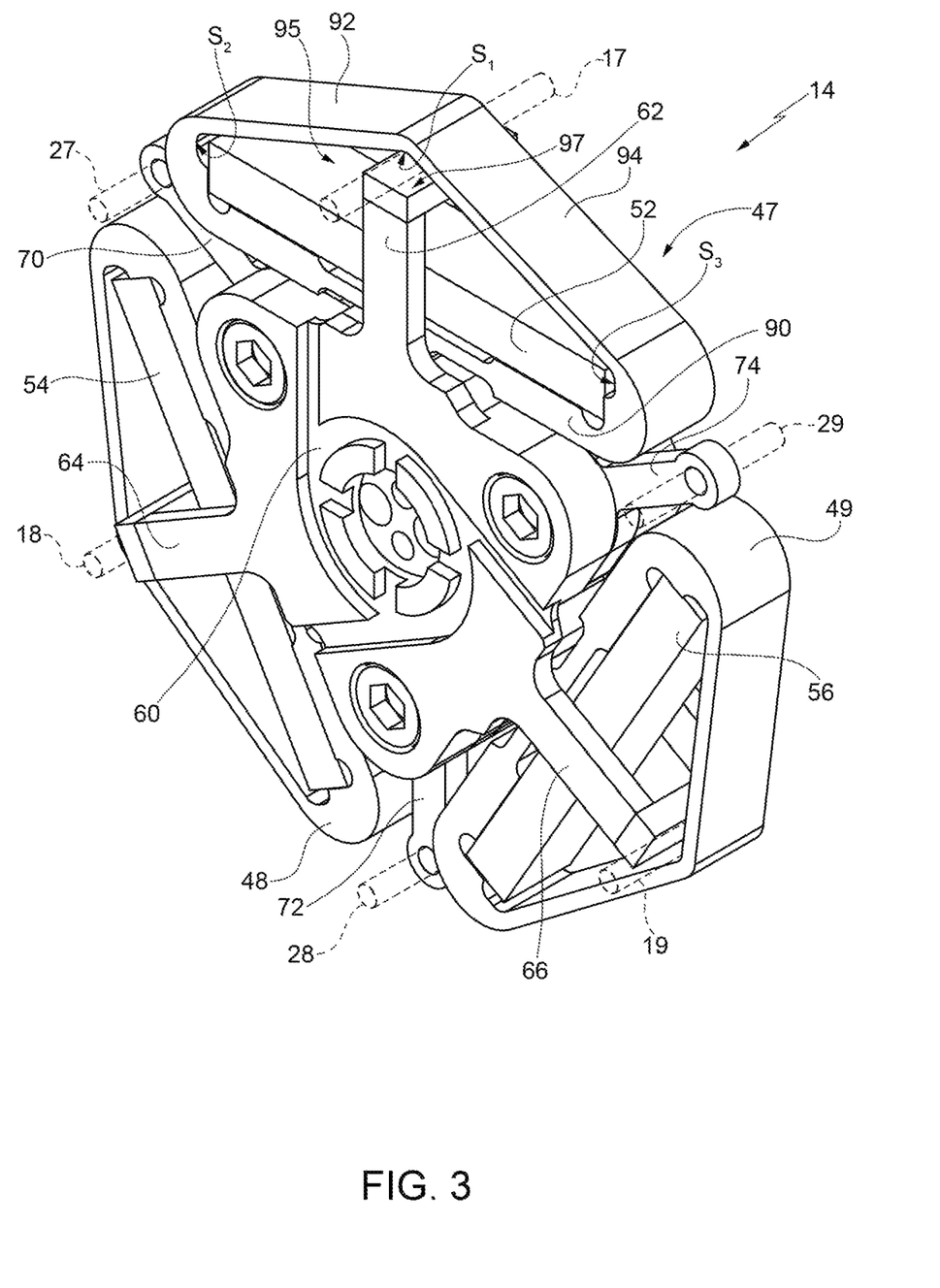
FIG. 3 shows an enlarged perspective view of a portion of the deployable structure shown in FIG. 1.

As shown in further detail in FIGS. 2 and 3, the first shape-locking element 14 comprises a first and a second substructure 44, 46, also symmetrical with respect to the axis of symmetry H.

The first substructure 44 comprises a first, a second and a third clamping element 47, 48, 49, which have the same shape and are arranged so as to form angles of 120°, i.e. at the vertexes of a hypothetical equilateral triangle. Furthermore, the first substructure 44 comprises a first, a second and a third piezoelectric device 52, 54, 56, identical to one another and operatively coupled, respectively, to the first, second and third clamping element 47, 48, 49, as described in greater detail below, with reference only to the first clamping element 47, since the pairs formed i) of the first clamping element 47 and the first piezoelectric device 52, ii) of the second clamping device 48 and the second piezoelectric device 54, and iii) of the third clamping element 49 and the third piezoelectric device 56 are identical to one another.

The second substructure 46 comprises a central body 60, from which a first, a second and a third arm 62, 64, 66 identical to one another, and a first, a second and a third supporting element 70, 72, 74 identical to one another, depart radially, i.e. perpendicularly relative to the axis of symmetry H.

In particular, the first, the second and the third arm 62, 64, 66, are arranged angularly so that adjacent pairs of them form angles of 120°; furthermore, also the first, the second and the third supporting element 70, 72, 74 are arranged angularly so that adjacent pairs of them form angles of 120°. In addition, the group formed of the first, second and third supporting element 70, 72, 74 is angularly staggered by 60° relative to the unit formed of the first, second and third arm 62, 64, 66. Therefore, the first supporting element 70 is interposed between the first and the second arm 62, 64, from which it is spaced by 60°; the second supporting element 72 is interposed between the second and the third arm 64, 66, from which it is spaced by 60°; lastly, the third supporting element 74 is interposed between the first and the third arm 62, 66, from which it is spaced by 60°.

The first, the second and the third supporting element 70, 72, 74 form a first, a second and a third eyelet 80, 82, 84 respectively, which are evenly spaced from the axis of symmetry H; furthermore, pairs of adjacent eyelets from among the first, the second and the third eyelet 80, 82, 84 are angularly spaced from one another by 120°. The fourth, the fifth and the sixth rod 27, 28, 29 pass inside the first, second and third eyelet 80, 82, 84 respectively; said rods can slide relative to the corresponding eyelets. Therefore, the first shape-locking element 14 is mechanically coupled in a slidable manner to the second coupling structure 26 which, as described below, can act as a guide for movement of the first shape-locking element 14.

Again with reference to the first, second and third clamping element 47, 48, 49, the first clamping element 47 and the relative coupling with the first rod 17 are described below, by way of example. The second and the third clamping element 48, 49 are identical to the first clamping element 47; furthermore, the relative arrangements relative to the second and third rod 18, 19 are analogous to what is described below.

In detail, the first clamping element 47 has, to a first approximation, the shape of a hollow right prism, with the axis parallel to the axis of symmetry H and with the base in the shape of an isosceles triangle with rounded vertexes.

In greater detail, the first clamping element 47 is formed of a first lateral wall 90, which forms the base of the above-mentioned isosceles triangle, and a second and a third lateral wall 92, 94, which form the sides of the above-mentioned isosceles triangle.

The second and third lateral wall 92, 94 form a sort of rounded dihedron, since the respective inner surfaces are joined by means of a first curved surface $S_1$.

The inner surface of the first lateral wall 90 defines a base surface $S_b$, on which the first piezoelectric device 52 rests. Furthermore, the first lateral wall 90 forms a first and a second shoulder, which define a first and a second lateral shoulder surface $S_{s1}$, $S_{s2}$ respectively, which are arranged perpendicularly relative to the base surface $S_b$; the first piezoelectric device 52 is arranged between the first and the second lateral shoulder surface $S_{s1}$, $S_{s2}$, in direct contact. In other words, the first piezoelectric device 52 is arranged in a sort of hollow formed in the first lateral wall 90.

The second and third lateral wall 92, 94 are joined to the first and the second lateral shoulder surface $S_{s1}$, $S_{s2}$ respectively by means of a second and third curved surface $S_2$, $S_3$ respectively, which have a concavity facing towards the inside.

In greater detail, the first clamping element 47 is fixed to the central body 60 in a per se known manner and forms a cavity 95. Furthermore, the first piezoelectric device 52 has an elongated shape parallel to the first lateral wall 90, with which it is in direct contact. In addition, the first piezoelectric device 52 can be electrically controlled to operate alternatively:

i) in a rest mode (illustrated in FIGS. 2 and 3), in which the first piezoelectric device 52 has a first length (measured along its direction of elongation), said first length being such that the ends of the first piezoelectric device 52 do not contact the second and third curved surface $S_2$, $S_3$; and ii) in an active mode (not shown), in which the first piezoelectric device 52 has a second length, greater than the first length and such that the ends of the first piezoelectric device 52 exert a force on the first and second lateral shoulder surface $S_{s1}$, $S_{s2}$.

As shown in FIG. 3, the first arm 62 has a shape such as to surround both the first wall 90 and the first piezoelectric device 52. Furthermore, taking the axis of symmetry H as a reference, the first arm 62 forms a supporting surface 97, which is parallel to the axis of symmetry H and stands above, at a distance, the first piezoelectric device 52 which, as said, stands above the first lateral wall 90. In practice, the supporting surface 97 is parallel to the axis of the first clamping element 47 and delimits, together with the first curved surface $S_1$, a portion of space of the cavity 95, inside which the first rod 17 extends; said portion of space will be referred to below as the housing portion.

In greater detail, when the first piezoelectric device 52 is in rest mode, the distance between the supporting surface 97 and the first curved surface $S_1$ is such that the first rod 17 can slide relative to said surfaces, therefore can slide relative to the first shape-locking element 14. On the contrary, when the first piezoelectric device 52 is in active mode, a reduction in the distance occurs between the supporting surface 97 and the first curved surface $S_1$, with respect to the distance in the rest mode; said reduction is due to the elastic deformations of the first, second and third lateral wall 90, 92, 94, caused by the force exerted by the first piezoelectric device 52 on the first and on the second lateral shoulder surface $S_{s1}$, $S_{s2}$.

More specifically, when the first piezoelectric device 52 is in active mode, the supporting surface 97 and the first curved surface $S_1$ exert a force on the first rod 17 such that the latter is clamped by the first clamping element 47, i.e. it is fixed to the latter.

As previously explained, the second and third rod 18, 19 couple with the second and third clamping element 48, 49 respectively in the same way in which the first rod 17 couples with the first clamping element 47. Therefore, the second and third rod 18, 19 can alternatively slide, or be fixed, to the second and third clamping element 48, 49 respectively, according to the operating mode of the second and third piezoelectric device 54, 56 respectively. Furthermore, the second and third clamping element 48, 49 define corresponding housing portions, inside which the second and third rod 18, 19 extend respectively.

The housing portions of the first, second and third clamping elements 47, 48, 49, and therefore also the corresponding rods, are evenly spaced from the axis of symmetry H and are angularly arranged in such a way that adjacent pairs thereof (and therefore also adjacent pairs of the corresponding rods) are spaced from each other by 120°. Furthermore, angularly, the first, fourth, second, fifth, third and sixth rod 17, 27, 18, 28, 19, 29 are arranged in sequence; furthermore, angularly, adjacent rods are spaced from each other by 60°.

Below it is assumed that the first, the second and the third piezoelectric device 52, 54, 56, and more generally the piezoelectric devices of the first robotic system 4, are always controlled in the same operating condition, therefore for the sake of brevity reference will be made only to the operating condition of the first piezoelectric device 52. Furthermore, reference will be made to the unlocked state to indicate the situation in which the first coupling structure 16 can slide relative to the first shape-locking element 14, and to the locked state to indicate the situation in which the first coupling structure 16 is locked by the first shape-locking element 14, and is therefore fixed (in a releasable manner) to the latter.

In the central body 60 of the first shape-locking element 14 two operating holes 100 of the through type are formed, by way of example, adapted to house electrical cables (not shown) connected to the first, second and third piezoelectric device 52, 54, 56, in order to allow control of the latter.

In the central body 60 a first and a second connection hole 102, 104, of through type, are also formed. The pair of operating holes 100 and the first and second connection hole 102, 104 are arranged preferably symmetrically around the axis of symmetry H and extend parallel to the latter.

The first connection cable 40 extends inside the first connection hole 102; said cable is fixed locally to the central body 60, in a per se known manner; in other words, at least one point of the first connection cable 40 is fixed to the central body 60. The first connection cable 40 therefore cannot slide relative to the first shape-locking element 14.

The second connection cable 42 extends inside the second connection hole 104; said second connection cable 42 is not fixed to the central body 60 and can therefore slide inside the second connection hole 104. In this regard it is observed that, strictly speaking, the presence of the first and second connection cable 40, 42 reduces the (otherwise perfect) symmetry of the deployable structure 2 around the axis of symmetry H. Nevertheless, for greater clarity, the expression "axis of symmetry" is maintained, valid to a first approximation. Variations are possible, however (not shown or further described) in which the first and second connection cable 40, 42 are replaced by corresponding pluralities of connection cables, arranged symmetrically around the axis of symmetry H; for example, for each robotic system three connection cables can be used, arranged symmetrically relative to the axis of symmetry H.

In relation to the second shape-locking element 24, as previously mentioned it has the same shape as the first shape-locking element 14, but is rotated 180° relative to the latter. The second shape-locking element 24 is shown in greater detail in FIG. 4, where for the sake of visual simplicity only some of the respective components are indicated, with the same reference numbers as those previously used to indicate the corresponding components of the first shape-locking element 14, unless specified otherwise.

Figure 4:
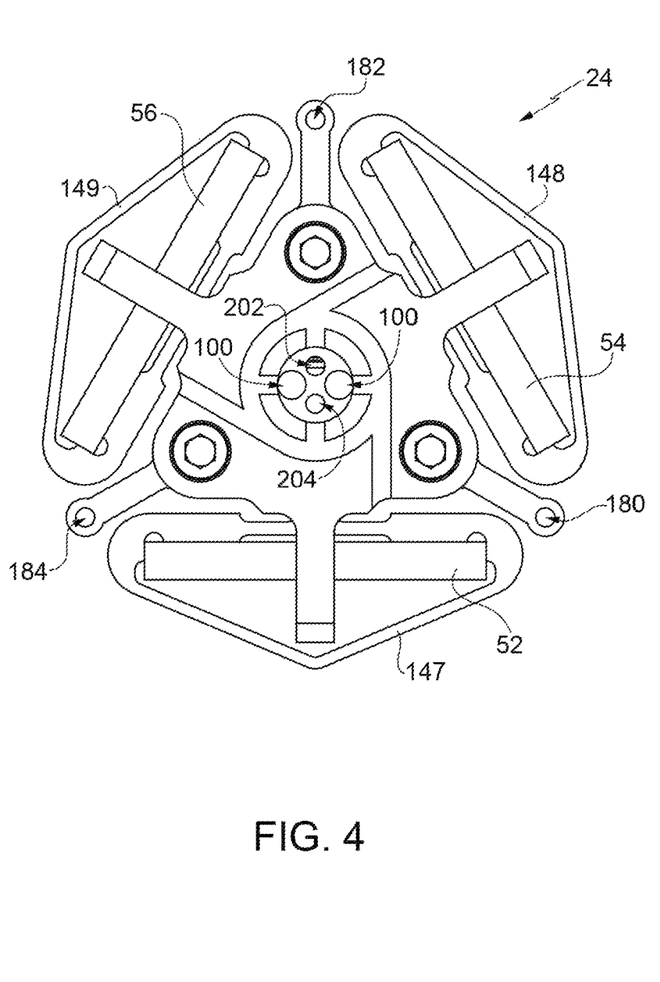

In greater detail, the three eyelets of the second shape-locking element 24 will be referred to below as the fourth, fifth and sixth eyelet respectively (indicated by 180, 182 and 184 respectively). The third rod 19, the first rod 17 and the second rod 18 pass through the fourth, the fifth and the sixth eyelet 180, 182, 184 respectively; said rods can slide relative to the corresponding eyelets. Therefore, the second shape-locking element 24 is mechanically coupled in a slidable manner to the first coupling structure 16, which, as described below, can act as a guide for the movement of the second shape-locking element 24.

In addition, the first, second and third clamping element (indicated by 147, 148, 149 respectively) of the second shape-locking element 24 mechanically couple with the fifth rod 28, the sixth rod 29 and the fourth rod 27 respectively. Furthermore, analogously to what was described previously for the first shape-locking element 14, the fourth, fifth and sixth rod 27, 28, 29 can slide alternatively, or be fixed, respectively, to the third, to the first and to the second clamping element 149, 147, 148 of the second shape-locking element 24, according to the operating mode of the third, the first and the second piezoelectric device 56, 52, 54 respectively of the second shape-locking element 24. Below it is assumed that the first, the second and the third piezoelectric device 52, 54, 56 of the second shape-locking element 24, and more generally the piezoelectric devices of the second robotic system 6, are always controlled in the same operating condition, therefore for the sake of brevity reference will be made only to the operating condition of the first piezoelectric device 52 of the second shape-locking element 24. Furthermore, reference will be made to the unlocked state to indicate the situation in which the second coupling structure 26 can slide relative to the second shape-locking element 24, and to the locked state to indicate the situation in which the second coupling structure 26 is locked by the second shape-locking element 24, and is therefore fixed (in a releasable manner) to the latter.

The second shape-locking element 24 has, among other things, also the above-mentioned first and second connection hole, indicated by 202 and 204. The second connection cable 42, which is locally fixed to the second shape-locking element 24, in a per se known manner, extends inside the first connection hole 202; the second connection cable 42 therefore cannot slide relative to the second shape-locking element 24.

The first connection cable 40 extends inside the second connection hole 204, and can slide inside said second connection hole 204.

As previously mentioned, due to the shape of the first and second shape-locking element 14, 24 and to the above-mentioned staggering by 180°, the deployable structure 2 allows a respective rest condition in which the first, second, third, fourth, fifth and sixth rod 17, 18, 19, 27, 28, 29 are straight. In this regard, as shown respectively in FIGS. 5 and 6, the first and the second distal element 12, 22 are adapted to allow the above-mentioned rest condition of the deployable structure.

Figure 5:
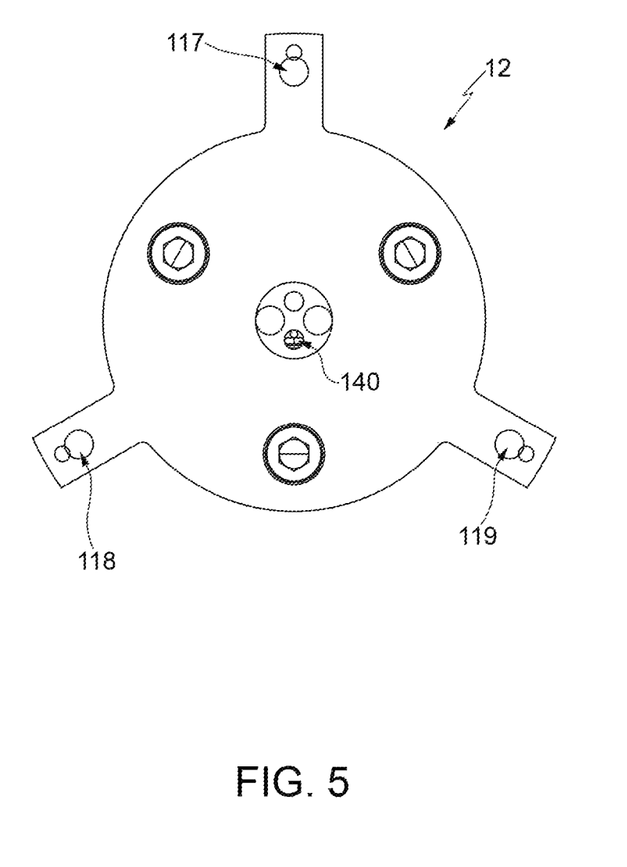

In detail, the first distal element 12 has a first, a second and a third fixing seat 117, 118, 119, of known type. The ends of the first, second and third rod 17, 18, 19 are fixed respectively, as previously mentioned, in the first, in the second and in the third fixing seat 117, 118, 119, which are evenly spaced from the axis of symmetry H; adjacent pairs of fixing seats are angularly spaced by 120°. Furthermore, the first distal element 12 comprises a fourth fixing seat 140, in which one end of the first connection cable 40 is fixed.

When the deployable structure 2 is in the rest condition, the first, the second and the third fixing seat 117, 118, 119 are aligned with the corresponding housing portions formed by the first, the second and the third clamping element 47, 48, 49 of the first shape-locking element 14; furthermore, the fourth fixing seat 140 is aligned with the first connection hole 102 of the first shape-locking element 14.

Figure 6:
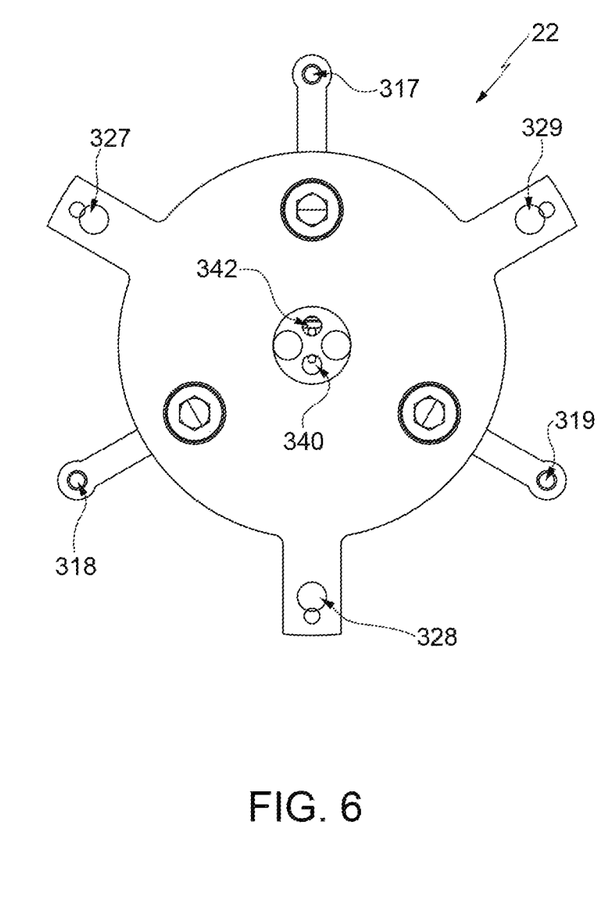

The second distal element 22 forms a fifth, a sixth and a seventh fixing seat 327, 328, 329, in which corresponding ends of the fourth, fifth and sixth rod 27, 28, 29 are respectively fixed. Furthermore, the second distal element 22 comprises a seventh, an eighth and a ninth eyelet 317, 318, 319, which are evenly spaced from the axis of symmetry H and are arranged so that adjacent pairs thereof are angularly spaced by 120°. The first, second and third rod 17, 18, 19 slide inside the seventh, eighth and ninth eyelet 317, 318, 319 respectively.

Therefore, the second distal element 22 is mechanically coupled in a slidable manner with the first coupling structure which, as described below, can act as a guide for the movement of the second distal element 22.

In addition, the second distal element 22 forms an eighth fixing seat 342, in which one end of the second connection cable 42 is fixed, and a further hole 340, which will be referred to below as the through hole; the first connection cable 40 runs inside the through hole 340.

When the deployable structure 2 is in the rest condition, the seventh, eighth and ninth eyelet 317, 318, 319 are respectively aligned with the housing portions defined by the first, second and third clamping element 47, 48, 49 of the first shape-locking element 14; furthermore, the fifth, sixth and seventh fixing seat 327, 328, 329 are respectively aligned with the first, second and third eyelet 80, 82, 84 of the first shape-locking element 14. The through hole 340 and the eighth fixing seat 342 are respectively aligned with the first and the second connection hole 102, 104 of the first shape-locking element 14.

Figure 7:
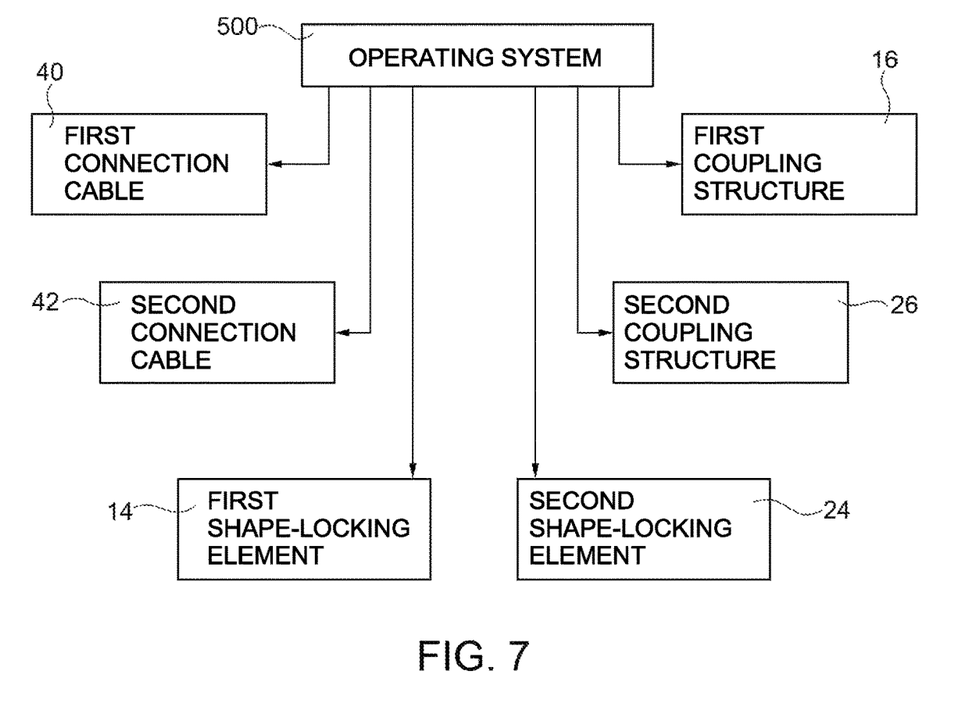
FIG. 7 shows a block diagram which illustrates connections between components of the present deployable structure.

As shown in FIG. 7, the deployable system 1 comprises an operating system 500, which is operatively coupled with the first and second coupling structure 16, 26 and with the shape-locking elements of the first and second robotic system 4, 6 (FIG. 7 shows for the sake of simplicity only the first and second shape-locking element 14, 24), and with the first and second connection cable 40, 42.

In particular, the operating system 500 is able to move each of the first, second, third, fourth, fifth and sixth rod 17, 18, 19, 27, 28, 29, and each of the connection cables 40, 42, for example by means of a corresponding linear electric motor (not shown) coupled with it. Furthermore, the operating system 500 is able to control, as previously mentioned, the state of each shape-locking element; for said purpose, the operating system 500 is electrically connected to the piezoelectric devices, for example by means of the above-mentioned electric cables (not shown) which extend into the operating holes.

Below it is assumed that, as previously mentioned, at each instant all the shape-locking elements of the first robotic system 4 are controlled in the same state (locked/unlocked), therefore reference will be made only to the state of the first shape-locking element 14; similarly, it is assumed that at each instant all the shape-locking elements of the second robotic system 6 are controlled in the same state, therefore reference will be made only to the state of the second shape-locking element 24. Furthermore, it is assumed that each of the rods of each of the first and the second coupling structure 16, 26 has a compression resistance such as to allow the rod to withstand the force which the operating system 500 exerts on it to cause deployment of the deployable structure 2; in this regard, each of the rods of each of the first and second coupling structure 16, 26 can be made, for example, of nitinol. The first and the second cable 40, 42 are adapted to withstand tensile stress, but substantially yield to compression and bending.

Below, the operations are described that allow deployment of the deployable structure 2, with reference to FIGS. 8-13 in which, for the sake of visual simplicity, the components of the first and second robotic system 4, 6 have simplified forms compared to the preceding description. In other words, FIGS. 8-13 show a simplified deployable structure for the sole purpose of describing the deployment principle.

Figure 8:
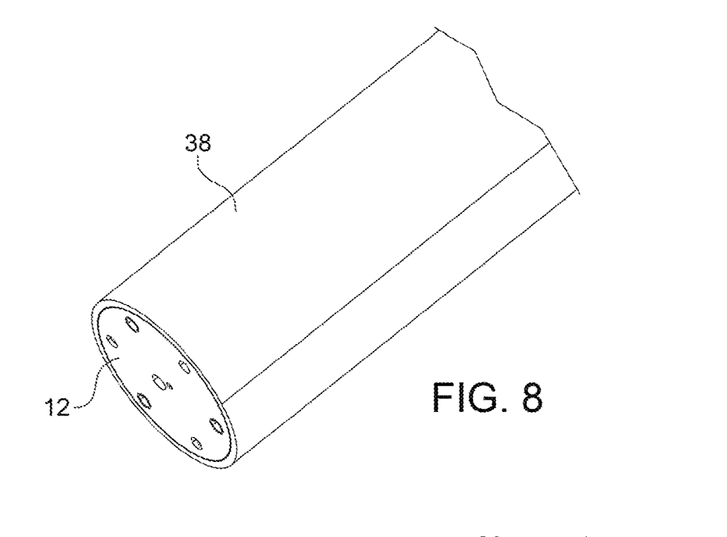
FIGS. 8-13 show perspective views of a simplified version of the present deployable structure, during successive steps of the deployment process.

Initially, as shown in FIG. 8, the first and the second robotic system 4, 6 are arranged inside the housing structure 38. In these conditions, although not shown, the second distal element 22 contacts the first distal element 12; furthermore, the first shape-locking element 14 contacts the second shape-locking element 24. Furthermore, the first and the second shape-locking element 14, 24 are both locked. In addition, inside the housing structure 38, the first and the second robotic system 4, 6 are arranged in such a way that the first and the second connection cable 40, 42 are extended.

Figure 9:
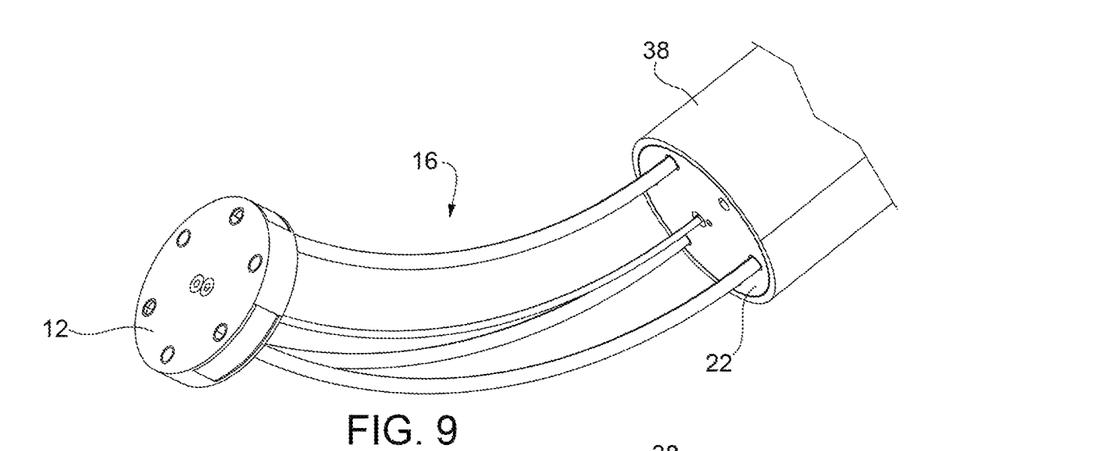

Subsequently, as shown in FIG. 9, the operating system 500 unlocks the first shape-locking element 14 and moves the first distal element 12, moving at least one of the first, second and third rod 17, 18, 19, and at the same time maintaining the second shape-locking element 24 locked. In this way, the first distal element 12 moves away from the second distal element 22, along a first portion of a desired curved trajectory. In greater detail, an elastic deformation of the first coupling structure 16 occurs, under the action of the operating system 500.

Figure 10:
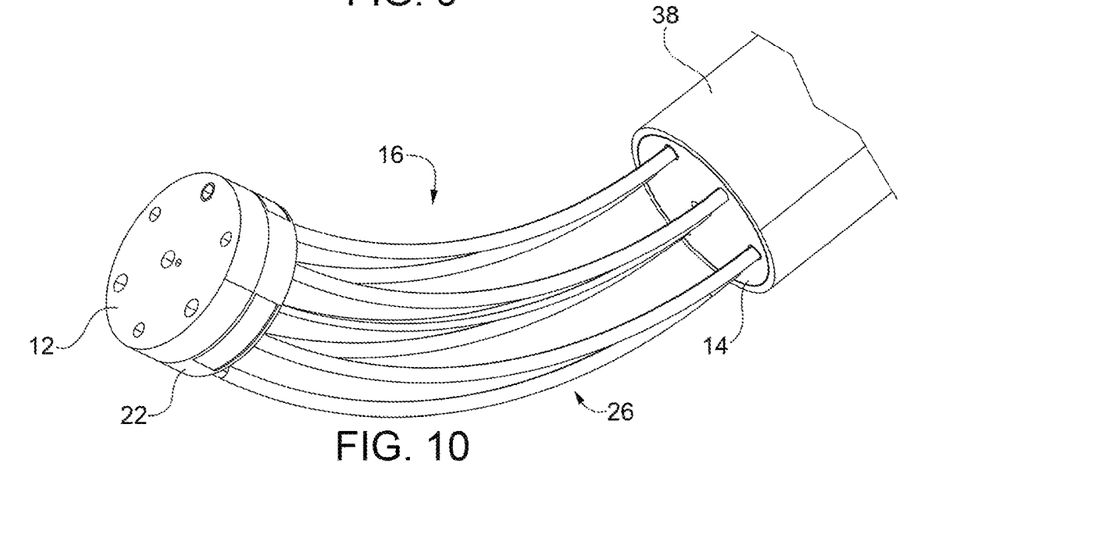

Subsequently, the operating system 500 locks the first shape-locking element 14; then the operating system 500 unlocks the second shape-locking element 24 and moves the second distal element 22, moving at least one of the fourth, fifth and sixth rod 27, 28, 29, thus causing an elastic deformation of the second coupling structure 26, and at the same time maintaining the first shape-locking element 14 locked, as shown in FIG. 10. In particular, the operating system 500 operates the second coupling structure 26 in a manner corresponding to the preceding operation of the first coupling structure 16, i.e. in such a way as to cause the second distal element 22 to follow the same first portion of trajectory as previously followed by the first distal element 12; for said purpose, the operating system 500 takes account of the differences between i) the reciprocal arrangement between the first distal element 12 and the first coupling structure 16, and ii) the reciprocal arrangement between the second distal element 22 and the second coupling structure 26. Furthermore, the first coupling structure 16 acts as a guide for the movement of the second distal element 22, guaranteeing that the latter actually follows the same first portion of trajectory as the one previously followed by the first distal element 12.

In greater detail, when the first robotic system 4 is unlocked, the latter, and therefore also the first coupling structure 16, has a first stiffness, which allows the first coupling structure 16 to elastically deform. Vice versa, when the first robotic system 4 is locked, the latter, and therefore also the first coupling structure 16, has a second stiffness, greater than the first stiffness. Said second stiffness allows the first coupling structure 16 to act as a guide for the movement of the second distal element 22, without the movement of the latter entailing a deformation (for example, a straightening) of the first coupling structure 16.

Figure 11:
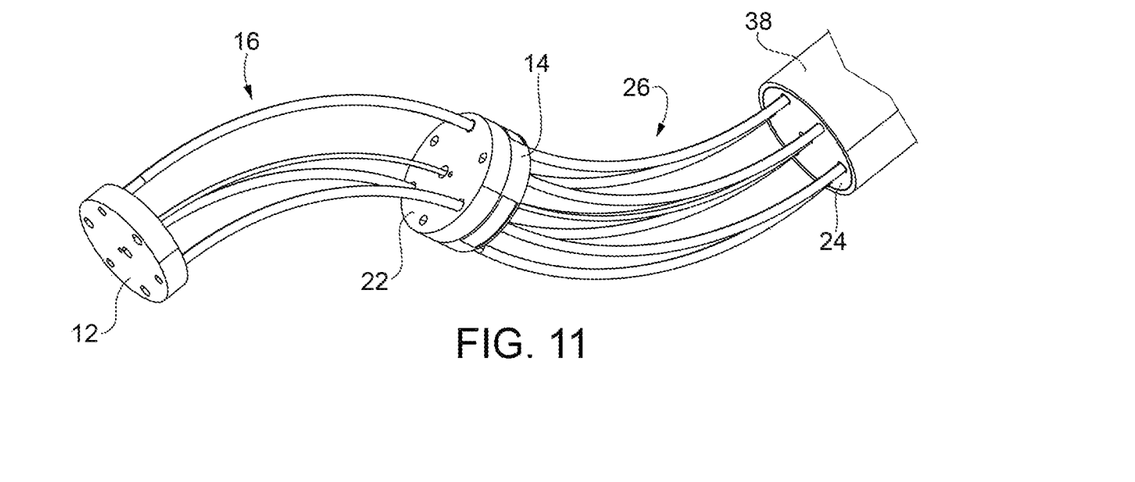

Subsequently, the operating system 500 locks the second shape-locking element 24 and then unlocks the first shape-locking element 14. The operating system 500 then operates the first coupling structure 16 and moves the first distal element 12 along a second portion of the desired trajectory, at the same time maintaining the second shape-locking element 24 locked. In this way, as shown in FIG. 11, the first distal element 12 moves away again from the second distal element 22, along the second portion of desired trajectory. In greater detail, a new elastic deformation of the first coupling structure 16 occurs, due to the action of the operating system 500. Furthermore, the first connection cable 40 causes the first distal element 12 to drag behind it the shape-locking elements of the first robotic system 4, and in particular the first shape-locking element 14, which follows the first portion of trajectory, guided by the second coupling structure 26, until contacting, if necessary, the second distal element 22.

Since the second robotic system 6 has the same behaviour as the first robotic system 4 in terms of stiffness, when the second robotic system 6 is unlocked, the latter, and therefore also the second coupling structure 26, can elastically deform. Vice versa, when the second robotic system 6 is locked, the latter, and therefore also the second coupling structure 26, has a stiffness such that the second coupling structure 26 acts as a substantially non-deformable guide for the movement of the first shape-locking element 14, and more generally for the shape-locking elements of the first robotic system 4.

Figure 12:
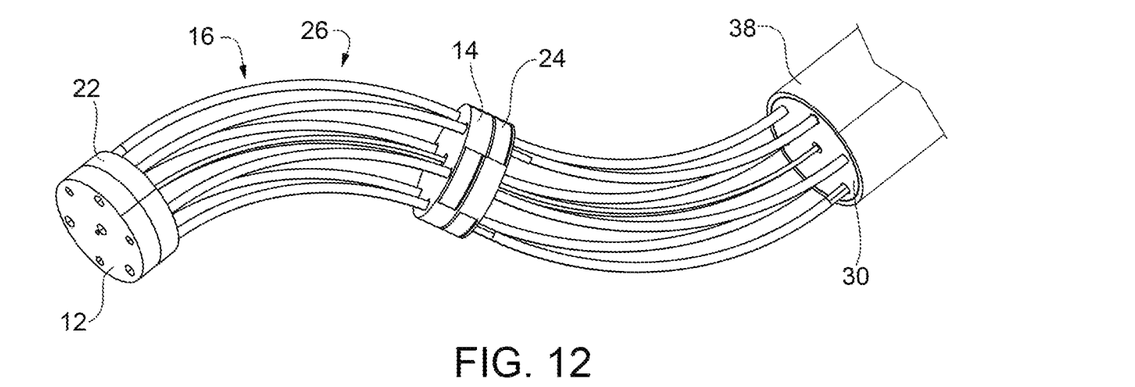

Subsequently, the operating system 500 locks the first shape-locking element 14; the operating system 500 then unlocks the second shape-locking element 24 and moves the second distal element 22, moving at least one of the fourth, fifth and sixth rod 27, 28, 29, and at the same time maintaining the first shape-locking element 14 locked. In particular, the operating system 500 operates the second coupling structure 26 in a manner corresponding to the previous operation of the first coupling structure 16, i.e. so as to cause the second distal element 22 to follow the same second portion of trajectory followed previously by the first distal element 12; at the same time, the second shape-locking element 24 is dragged by the second distal element 22 and follows the first portion of the trajectory. In this way, the second distal element 22 and the second shape-locking element 24 move, guided by the first coupling structure 16, if necessary until contacting the first distal element 12 and the first shape-locking element 14 respectively, as shown in FIG. 12.

Figure 13:
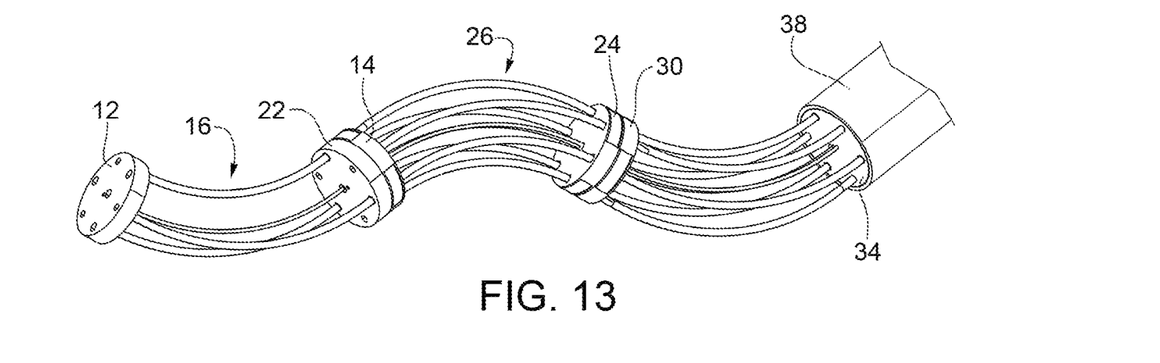

Subsequently, the operating system 500 locks the second shape-locking element 24 and then unlocks the first shape-locking element 14. Then, as shown in FIG. 13, the operating system 500 again moves the first distal element 12 along a third portion of the desired trajectory; the first distal element 12 drags the first shape-locking element 14, which follows the second portion of the trajectory, and the third shape-locking element 30, which follows the first portion of the trajectory. If necessary, the above operations can then be repeated, according to the desired trajectory and the number of shape-locking elements.

In practice, the first and the second robotic system 4, 6 are controlled in an alternating manner. In particular, when the first coupling structure 16 is unlocked, the second coupling structure 26 is locked; furthermore, when the second coupling structure 26 is unlocked, the first coupling structure 16 is locked.

In order to retract the deployable structure 2, the operating system 500 alternatively retracts the first and the second connection cable 40, 42; in particular, the robotic system that was deployed last in the deployment step is retracted first. During the retraction of a robotic system, simultaneously with retraction of the respective connection cable, the relative rods can also be retracted; for said purpose, the operating system 500 performs operations opposite to those performed in the deployment step. In this regard, as previously mentioned, each of the first and second connection cable 40, 42 operates substantially by traction, dragging the corresponding shape-locking elements, thus moving the robotic system to which it belongs. Any simultaneous retraction of the rods allows the distal elements to follow the trajectory in reverse with respect to the deployment so that, also in retraction, the unlocked robotic system does not disturb the locked one, which acts as a guide.

In practice, the first and the second robotic system 4, 6 are able to follow the same trajectory, both during the deployment and during retraction. Furthermore, although not shown, each of the distal elements and the shape-locking elements of the first and second robotic system 4, 6 can form one or more operating channels, inside which instruments can slide (not shown) characteristic of the application designed for the deployable system 1, for example optic fibres. For example, when the deployable structure 2 is in the rest condition, each channel can be formed of a plurality of respective holes aligned in succession and made in the first distal element 12, in the second distal element 22 and in the shape-locking elements respectively.

Figure 14:
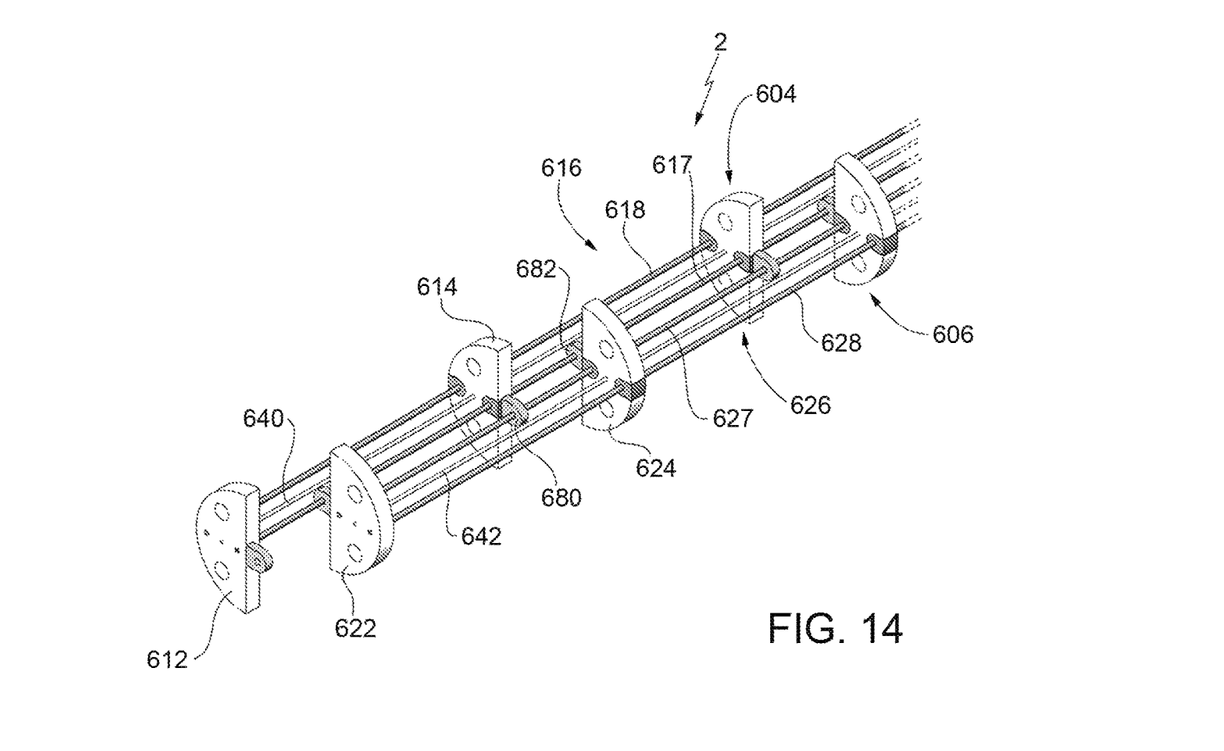
FIG. 14 shows a perspective view of a portion of a further embodiment of the present deployable structure.

According to a variation shown in FIG. 14, the first and the second robotic system (indicated by 604 and 606 respectively) are constrained to slide alongside each other.

Without any loss of generality, the first and the second coupling structure (indicated by 616 and 626 respectively) each include a pair of rods; in other words, the third and the sixth rod are absent. Furthermore, the rods of the first and the second coupling structure 616, 626 are arranged in a planar manner, in the following order: second rod (indicated by 618), first rod (indicated by 617), fourth rod (indicated by 627) and fifth rod (indicated by 628). FIG. 14 also shows the first and the second distal element (indicated by 612 and 622), the first and the second shape-locking element (indicated by 614 and 624) and the first and the second connection cable (indicated by 640 and 642).

The first shape-locking element 614 couples with the first coupling structure 616 in a controllable manner, so that each first and second rod 617, 618 is alternatively slidable relative to the first shape-locking element 614, or is fixed to the latter. Similarly, the second shape-locking element 624 couples with the second coupling structure 626 in a controllable manner, so that each fourth and fifth rod 627, 628 is alternatively slidable relative to the second shape-locking element 624, or is fixed to the latter.

The first shape-locking element 614 further forms a first coupling seat 680 in the form of an eyelet, inside which the fourth rod 627 slides; furthermore, the second shape-locking element 624 forms a second coupling seat 682 in the form of an eyelet, inside which the first rod 617 slides.

In practice, when the first robotic system 604 is locked, the stiffness of the first robotic system 604 is such that the first rod 617 acts as a substantially non-deformable guide for the movement of the second robotic system 606; similarly, when the second robotic system 606 is locked, the fourth rod 627 acts as a substantially non-deformable guide for the movement of the shape-locking elements of the first robotic system 604.

The advantages offered by the present deployable structure emerge clearly from the preceding description. In particular, the present deployable structure is intrinsically of the follow-the-leader type. Furthermore, the present deployable structure is of the continuum type, therefore it is without articulations and can follow curved trajectories with great accuracy, also in the presence of curves with relatively limited radii of curvature. Again, during deployment of the present structure, no vibrations are generated; furthermore, in each deployment step, the corresponding forward movement of the robotic system is not necessarily equal to a predefined value, but can be varied in a continuous manner, within a maximum value equal to the above-mentioned length $L_{max}$.

In addition, the use of a symmetrical configuration is advantageous, in particular when the first and the second robotic system are interlaced, since it allows reduction of the cross-section of the deployable structure, while the bending stiffness of each robotic system remains the same. Furthermore, the interlaced configuration allows the neutral bending axes associable with the first and second robotic system to coincide; in this way, the sliding of the unlocked robotic system relative to the locked robotic system can take place without significantly disturbing the form of the locked robotic system. The interlaced configuration therefore allows the deployable structure to be directed more accurately. Furthermore, the deployment and recovery of the first and second robotic system are performed on the basis of the same operating pattern.

Lastly, it is evident that modifications and variations can be made to the present deployable structure, without departing from the scope of the present invention, as defined by the attached claims.

For example, the number of shape-locking elements of the first and second robotic system 4, 6 can be different from what has been described. The number and form of the rods of the first and second coupling structure 16, 26 can be different from what has been described.

The forms, the arrangements and the couplings of the first, second and third clamping element 47, 48, 49, and of the first, second and third piezoelectric device 52, 54, 56 can be different from what has been described.

In relation to the coupling structures, each of them can be formed of a number of rods other than three. For example, if the deployable structure is designed for applications in a two-dimensional space, instead of a three-dimensional space, each coupling structure can include only two corresponding rods.

It is also possible for the controlled fixing of the first and second coupling structure 16, 26 to the corresponding shape-locking elements to be obtained without using piezoelectric devices. For example, each shape-locking element can comprise pneumatic and/or hydraulic actuators (not shown), to fix the corresponding coupling structure in a controlled manner. Again, purely by way of example, it is also possible for the controlled fixing to be obtained by using, inside the shape-locking elements, portions formed of shape-memory alloys.

What is claimed is:

1. A deployable structure comprising a first and a second robotic system, said first robotic system comprising:
   a first distal element;
   at least a first shape-locking element; and
   a first coupling structure, which mechanically couples the first distal element to the first shape-locking element and is operable in a first and a second operating condition;
   said second robotic system comprising:
      a second distal element;
      at least a second shape-locking element; and
      a second coupling structure, which mechanically couples the second distal element to the second shape-locking element and is operable in a first and a second operating condition; and wherein, when the first coupling structure operates in the first operating mode, said first coupling structure is elastically deformable and operable so as to move the first robotic system; and wherein, when the first coupling structure operates in the second operating mode, said first coupling structure forms a guide for the movement of the second robotic system; and wherein, when the second coupling structure operates in the first operating mode, said second coupling structure is elastically deformable and is operable so as to move the second robotic system; and wherein, when the second coupling structure operates in the second operating mode, said second coupling structure forms a guide for the movement of the first shape-locking element; and
   wherein said first shape-locking element comprises:
      a respective first substructure coupled with the first coupling structure so as to be alternatively slidable or fixed relative to the first coupling structure; and
      a respective second substructure coupled in slidable manner with the second coupling structure; and
   wherein said second shape-locking element comprises:
      a respective first substructure coupled with the second coupling structure so as to be alternatively slidable or fixed relative to the second coupling structure; and
      a respective second substructure coupled in a slidable manner with the first coupling structure.

2. The structure according to claim 1, wherein the first robotic system has a first and a second stiffness, when the first coupling structure operates respectively in the first and in the second operating mode, the second stiffness being greater than the first stiffness; and wherein the second robotic system has a third and a fourth stiffness, when the second coupling structure operates respectively in the first and in the second operating mode, the fourth stiffness being greater than the third stiffness.

3. The structure according to claim 2, wherein said second stiffness is such that, when the second robotic system moves with respect to the first robotic system, said first coupling structure substantially does not deform; and wherein said fourth stiffness is such that, when the first robotic system moves with respect to the second robotic system, said second coupling structure substantially does not deform.

4. The structure according to claim 2, wherein, when the first coupling structure operates in the first operating mode, said first coupling structure is slidable with respect to the first shape-locking element, and wherein, when the first coupling structure operates in the second operating mode, said first coupling structure is fixed to the first shape-locking element; and wherein, when the second coupling structure operates in the first operating mode, said second coupling structure is slidable with respect to the second shape-locking element, and wherein, when the second coupling structure operates in the second operating mode, said second coupling structure is fixed to the second shape-locking element.

5. The structure according to claim 2, wherein the first coupling structure comprises a first number of corresponding elongated elements and wherein the second coupling structure comprises a second number of corresponding elongated elements, said first and second number being at least two.

6. The structure according to claim 5, wherein the first shape-locking element comprises a number of respective locking elements, each locking element of the first shape-locking element being mechanically coupled to a corresponding elongated element-of the first coupling structure and including a corresponding piezoelectric device controllable in such a way that said corresponding elongated element is movable with respect to said locking element, or is fixed to said locking element; and wherein the second shape-locking element comprises a number of respective locking elements, each locking element of the second shape-locking element being mechanically coupled to a corresponding elongated element of the second coupling structure and including a corresponding piezoelectric device controllable in such a way that said corresponding elongated element of the second coupling structure is movable with respect to said locking element of the second shape-locking element, or is fixed to said locking element of the second shape-locking element.

7. The structure according to claim 5, wherein the second robotic system is mechanically coupled in a slidable way to at least one of the elongated elements of the first coupling structure; and wherein the first robotic system is mechanically coupled in a slidable way to at least one of the elongated elements of the second coupling structure.

8. The structure according to claim 7, wherein the first shape-locking element is mechanically coupled in a slidable way to at least one of the elongated elements of the second coupling structure; and wherein the second shape-locking element is mechanically coupled in a slidable way to at least one of the elongated elements of the first coupling structure.

9. The structure according to claim 5, wherein the first coupling structure comprises a first, a second and a third elongated element and wherein the second coupling structure comprises a fourth, a fifth and a sixth elongated element.

10. The structure according to claim 5, wherein the elongated elements of the first coupling structure are constrained to the first distal element and to the first shape-locking element so as to be arranged symmetrically with respect to an axis (H) and angularly evenly spaced; and wherein the elongated elements of the second coupling structure are constrained to the second distal element and to the second shape-locking element so as to be arranged symmetrically with respect to said axis and angularly evenly spaced.

11. The structure according to claim 10, wherein the first and the second robotic system are arranged coaxially; and wherein the elongated elements of the first coupling structure are angularly staggered with respect to the elongated elements of the second coupling structure.

12. The structure according to claim 1, wherein the first robotic system comprises a first connection element having an elongated shape, configured to operate in traction and fixed to the first distal element and to the first shape-locking element; and wherein the second robotic system comprises a second connection element having an elongated shape, configured to operate in traction and fixed to the second distal element and to the second shape-locking element.

13. The structure according to claim 1, wherein the first and the second robotic system are interlaced.

14. A system comprising a deployable structure comprising a first and a second robotic system, said first robotic system comprising:
    a first distal element;
    at least a first shape-locking element; and
    a first coupling structure, which mechanically couples the first distal element to the first shape-locking element and is operable in a first and a second operating condition;
said second robotic system comprising:
    a second distal element;
    at least a second shape-locking element; and
    a second coupling structure, which mechanically couples the second distal element to the second shape-locking element and is operable in a first and a second operating condition; and wherein, when the first coupling structure operates in the first operating mode, said first coupling structure is elastically deformable and operable so as to move the first robotic system; and wherein, when the first coupling structure operates in the second operating mode, said first coupling structure forms a guide for the movement of the second robotic system; and wherein, when the second coupling structure operates in the first operating mode, said second coupling structure is elastically deformable and is operable so as to move the second robotic system; and wherein, when the second coupling structure operates in the second operating mode, said second coupling structure forms a guide for the movement of the first shape-locking element;
said first shape-locking element comprises:
    a respective first substructure coupled with the first coupling structure so as to be alternatively slidable or fixed relative to the first coupling structure; and
    a respective second substructure coupled in slidable manner with the second coupling structure; and
said second shape-locking element comprises:
    a respective first substructure coupled with the second coupling structure so as to be alternatively slidable or fixed relative to the second coupling structure; and
    a respective second substructure coupled in a slidable manner with the first coupling structure, and
an operating system configured to operate the first and the second coupling structure and to control the first and the second coupling structure so that, when the first coupling structure operates in the first operating mode, the second coupling structure operates in the second operating mode, and so that, when the second coupling structure operates in the first operating mode, the first coupling structure operates in the second operating mode.

15. The system according to claim 14, wherein the first robotic system comprises a first connection element having an elongated shape, configured to operate in traction and fixed to the first distal element and to the first shape-locking element; and wherein the second robotic system comprises a second connection element having an elongated shape, configured to operate in traction and fixed to the second distal element and to the second shape-locking element; and wherein the operating system is also configured to operate the first and the second connection element.

* * * * *